United States Patent [19]

Grimberg

[11] Patent Number: 5,128,141

[45] Date of Patent: Jul. 7, 1992

[54] ASSOCIATION OF PHYSIOLOGICALLY DOSED VITAMIN A AND OF VARIOUS ACTIVE PRINCIPLES HAVING A THERAPEUTICAL ACTIVITY

[76] Inventor: Georges S. Grimberg, 123 rue de l'Université, 75007 Paris, France

[21] Appl. No.: 532,706

[22] Filed: Jun. 4, 1990

[30] Foreign Application Priority Data

Jun. 6, 1989 [FR] France ............... 89 07445

[51] Int. Cl.$^5$ ............... A61K 9/48
[52] U.S. Cl. ............... 424/451; 424/94.2; 424/94.64; 424/195.1
[58] Field of Search ............... 424/451, 94.2, 520, 424/93, 195.1, 94.64, 94.2

[56] References Cited

U.S. PATENT DOCUMENTS 4,604,234  8/1986  Fujii et al. ............... 424/642
4,970,080  11/1990  Laurent et al. ............... 424/684

Primary Examiner—Thurman K. Page
Assistant Examiner—Leon R. Horne
Attorney, Agent, or Firm—Browdy and Neimark

[57] ABSTRACT

The association of physiologically dosed vitamin A and of various active principles having a therapeutical activity such as mineral and/or organic sulphur, associated or not with biologically active principles such as dead yeast, lactobacilli, gastro-intestinal germs or others, dead or attenuated, characterized in that the vitamin A dose per capsule for the adult is at most 1700 I.U.

10 Claims, No Drawings

ASSOCIATION OF PHYSIOLOGICALLY DOSED VITAMIN A AND OF VARIOUS ACTIVE PRINCIPLES HAVING A THERAPEUTICAL ACTIVITY

FIELD OF THE INVENTION

Therapeutical compositions based on natural synthetic vitamin A are already known, these compositions also including sufficient quantities of mineral or organic sulphur, living yeast and sometimes a conveying excipient which can be made aromatic.

This is particularly the case of pharmaceutical compositions disclosed in FR - A - 2 228 470, in which, however, the vitamin A quantity is in too large a proportion to ensure safety. Thus, by continuously exceeding the daily needs of vitamin A, vitamin A accumulates in the tissues and in some cases causes severe disturbances.

Thus, the use of such pharmaceutical compositions is more and more prohibited by the various Ministries granting the authorizations for putting the drugs on the market.

By very serious studies, it has now been possible to obtain surprising results with small doses of vitamin A, viz, of the order of 10 to 12 times less than in the preceding cases.

Moreover, it has also been discovered that the living yeast previously used was not always used judiciously and, therefore, the use of a dead yeast which does not cause the same secondary reactions and therefore is better tolerated by the patient has now been provided.

Following these studies about which further details will be given hereafter, it has been possible to develop a new therapeutically active drug, adapted for remedying and improving disorders of otorhinolaryngology, of dermatology, of rheumetology, of the intestinal flora, and which in a more general manner has an immuno-stimulating humoral and tissue level activity.

Therefore, the result of this new drug is to provide the patient's system with an enhanced ability of defending itself a broken equilibrium and by reestablishing proper body functioning particularly the good tissue operation of the various organs, by allowing the recovery of certain deviant or discontinued functions, by providing anti-infectious, and this in spite of the fact that the doses of natural or synthetic vitamin A are very small. Thus, treatment with the new pharmaceutical composition can be carried out for a very long period to accomplish the aforementioned objectives and without danger of causing a toxic build-up of vitamin A.

Conditions for which this new drug may be prescribed are rhinotubal catarrh, chronic otorrhea, inner ear deafness, operated ostospongiosis accompanied by tubal catarrh, otititis glue, chronic amygdalitis, chronic purulent rhinitis, sinustitis, recurrent rhinopharyngitis, acne, ungual alternation, constipation, diarrhea, and stimulation if immunity alone or in association with a vaccination.

OBJECTS AND SUMMARY OF THE INVENTION

According to an object of the invention, the dose of vitamin A per capsule for an adult is 1700 I.U.

According to another feature of the invention, the dose of vitamin A per capsule for a baby is 1000 I.U.

According to a second object of the invention, the formula of the capsule for the adult is:

| | |
|---|---|
| Vitamin A | 1700 I.U. |
| Base L cystine | 72.6 mg |
| Washed sublimed sulphur | 22 mg |
| Dead yeast | 77.4 mg |

According to a third object of the invention, the formula of the capsule for a baby is:

| | |
|---|---|
| Vitamin A | 1000 I.U. |
| Base L cystine | 72.6 mg |
| Washed sublimed sulphur | 22 mg |
| Dead yeast | 77.4 mg |

Various other features of the invention will become more apparent from the following detailed description.

DETAILED DESCRIPTION OF THE INVENTION

By way of information, it si pointed out that it is possible in some cases to use a capsule dosed differently and intended either for the chile from 30 months to 15 years or for the adult, meaning that in some cases one has:

| | |
|---|---|
| Vitamin A | 1500 I.U. |
| Base L cystine | 72.6 mg |
| Washed sublimed sulphur | 22 mg |
| Dead yeast | 77.4 mg |

In order to have a more precise indication on the therapeutical tolerance of these three formulas, a double blind study was made by using the formula against a placebo on 123 children with two capsules per day for three months.

It should be pointed out that the active formula per capsule was:

| | |
|---|---|
| Vitamin A | 1500 I.U. |
| Base L cystine | 72.6 mg |
| Washed sublimed sulphur | 22 mg |
| Dead yeast | 77.4 mg |

In some cases, it may be necessary to introduce in a variable quantity mineral sulphur, organic sulphur (cystine or other), a biologically active principle (dead yeast, lactobacilli or gastrointestinal micro-organisms or other dead and/or attenuated micro-orgnanisms) in variable quantities in the formulas as a function of an accurate therapeutical action.

During the winter-spring period of 1987-1988, nine general practitioners under the authority of an otorhinolaryngology pediatrist, distributed throughout the French territory, administered the new drug to children who had come for medical advice on the otorhinolaryngology sphere. These children, with recurrent otorhinolaryngology infection past records, were well known and regularly followed by their physicians.

The treatment (with the new drug or with a placebo of same galenic presentation) was administered doubly blindly, with the posology of two doses per day for three consecutive months.

When each otorhinolaryngology infection occurred, the children were examined again, with at least one final consultation in April-May in order to establish the check-up for the whole elapsed period. During each visit, the physician noted the reason of the consultation and the corresponding diagnosis, the possible prescription of an antibiotic, bed rest and the number of days of rest.

123 children of an average age of 4 and a half years, with extremes in age varying from two to seven years, took part in the study. The duration of the follow-up, equal for the two groups treated, was of seventeen weeks on an average. The number of otorhinolaryngology infections was found to be significantly lower with children treated with the new drug, when compared with the children treated with placebo. Likewise, the number of antibiotic cures and the duration of school absences for an otorhinolaryngology reason were significantly smaller for the new drug group as compared with the placebo group. Finally, the physician global appreciation, quantified from 0 (no result) to 3 (very good result) was significantly better for the new drug. The tolerance of the children to the new drug was excellent.

As a conclusion, the new drug administered to children having an otorhinolaryngology infection reduces significantly the otorhinolaryngology infectious relapses.

The results are well established for the two placebo/active principles groups. The number of otorhinolaryngology infections, the number of antibiotic cures, the number of days of absence and their duration, are clearly in favor of the "active principles".

It is therefore clearly established, and this for the first time, that this formula, although it contains only a vitamin A posology covering the so-called physiological needs in vitamin A and not containing living yeast but a dead yeast, has a well established therapeutical action.

In general, the posology which is proposed is the following:

| Dose per day for an adult | three capsules |
| Dose per day for a child | one or two capsules between one month and 15 years, as a function of the age. |

I claim:

1. In a pharmaceutical composition in unit dosage capsule form consisting essentially of vitamin A, at least one microorganism and at least one source of sulphur, the improvement wherein
said microorganism is dead or attenuated and said vitamin A is present in an amount of 1000 to 1700 I.U.

2. A composition in unit dosage form according to claim 1, comprising 1500 I.U. of said vitamin A.

3. A composition in unit dosage form according to claim 1, comprising 1000 I.U. of said vitamin a.

4. A composition in unit dosage form according to claim 1, comprising 1700 I.U. of said vitamin A.

5. A pharmaceutical composition in unit dosage form according to claim 1 consisting essentially of:

| Vitamin A | 1700 I.U. |
| Base L cystine | 72.6 mg |
| Washed sublimed sulphur | 22 mg |
| Dead yeast | 77.4 mg |

6. A pharmaceutical composition in unit dosage form according to claim 1 consisting essentially of:

| Vitamin A | 1000 I.U. |
| Base L cystine | 72.6 mg |
| Washed sublimed sulphur | 22 mg |
| Dead yeast | 77.4 mg |

7. A pharmaceutical composition in unit dosage form according to claim 1 consisting essentially of:

| Vitamin A | 1500 I.U. |
| Base L cystine | 72.6 mg |
| Washed sublimed sulphur | 22 mg |
| Dead yeast | 77.4 mg |

8. A pharmaceutical composition in unit dosage form according to claim 1 wherein said microorganism consists essentially of dead yeast, dead or attenuated lactobacilli, dead or attenuated gastrointestinal microorganisms, or mixtures thereof.

9. In a method for the treatment of otorhinolaryngial inflammations comprising orally administering to a patient in need of said therapy a pharmaceutical composition in unit dosage form consisting essentially of vitamin A, at least one microorganism, and at least one source of sulphur, the improvement wherein
said microorganism is dead or attenuated and said vitamin A is present in an amount of 1000 to 1700 I.U.

10. A method according to claim 9 wherein said dead or attenuated microorganism is yeast, lactobacilli, or a gastrointestinal microorganism.

* * * * *